United States Patent
Aberg et al.

(10) Patent No.: US 8,557,846 B1
(45) Date of Patent: *Oct. 15, 2013

(54) MEDICINAL TREATMENT OF DERMAL DISEASES IN DOGS

(71) Applicant: Bridge Pharma, Inc., Sarasota, FL (US)

(72) Inventors: A. K. Gunnar Aberg, Sarasota, FL (US); Vincent B. Ciofalo, Branford, CT (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/739,090

(22) Filed: Jan. 11, 2013

Related U.S. Application Data

(60) Provisional application No. 61/717,240, filed on Oct. 23, 2012.

(51) Int. Cl.
*A61K 31/4535* (2006.01)
(52) U.S. Cl.
USPC .......................................... 514/324; 514/886
(58) Field of Classification Search
None
See application file for complete search history.

(56) References Cited

U.S. PATENT DOCUMENTS

| | | | |
|---|---|---|---|
| 3,682,930 | A | 8/1972 | Bourquin et al. |
| 4,659,716 | A | 4/1987 | Villani et al. |
| 5,595,997 | A | 1/1997 | Aberg et al. |
| 6,207,683 | B1 | 3/2001 | Aberg et al. |
| 7,226,934 | B1 | 6/2007 | Aberg et al. |
| 7,557,128 | B2 | 7/2009 | Aberg et al. |
| 2010/0105734 | A1 | 4/2010 | Aberg et al. |
| 2010/0130550 | A1 | 5/2010 | Aberg et al. |

FOREIGN PATENT DOCUMENTS

WO    WO 01/19367 A1 * 3/2001

OTHER PUBLICATIONS

Thomas, Proceeding of the North American Veterinary Conference, "Canine Atopic Dermatitis: Old and New Therapies", (2005), pp. 285-288.*
"Dog Skin Disorders" Wikipedia; 2 pages; http://en.wikipedia.orgiwiki/Dog_skin_disorders; printed Oct. 15, 2012.
Hiller et al.; "The ACVD Task Force on Canine Atopic Dermatitis (I): Incidence and Prevalence"; Veterinary Immunology and Immunopathology; 81; pp. 147-151; (2001).
Kennedy, G-R.; "Metabolism and Pharmacokinetics of Ketotifen in Children"; Research and Clinical Forums; 4; pp. 17-20; (1982).
Le Bigot et al.; "Metabolism of Ketotifen by Human Liver Microsomes_In Vitro Characterization of a Tertiary Amine Glucuronidation"; Drug Metabolism and Disposition; 11(6); pp. 585-589; (1983).
Nolte et al.; "Inhibition of Basophil Histamine Release by Methotrexate"; Agents Actions; 23; pp. 173-176; (1988) Abstract.
Ruben, Dawn; Diphenhydramine (Benadryl(R)); www.petplace.com/drug-library/diphenhydramine-benadryl/page1.aspx; 2 pages; printed Oct. 16, 2012.
"U.S. Pet Ownership Statistics"; by The Humane Society of the United States; www.humanesociety.org/issues/pet_overpopulation/facts/pet_ownership_statistics.html; 2 pages; printed Dec. 31, 2012.
Tonelli et al.; "A Bio-assay for the Concomitant Assessment of the Antiphlogistic and Thymolytic Activities of Topically Applied Corticoids"; Endocrinology; 77; pp. 625-634; (1964).
"Dogs with Atopic Dermatitis: Causes, Diagnosis, and Treatment"; from WebMD http://pets.webmd.com/dogs/dogs-atopic-dermatitis-causes-diagnosis-treatment; 3 pages; printed Dec. 31, 2012.
Wauquier et al.; "Further Studies on the Distinctive Sleep-Wakefulness Profiles of Antihistamines (Astemizole, Ketotifen, Terfenadine) in Dogs"; Drug Development Research; 4; pp. 617-625; (1984).
Maclay et al.; "Postmarketing Surveillance: Practical Experience With Ketotifen"; British Medical Journal; 288; pp. 911-914 (1984).
Prowse, Keith; "Ketotifen in Adult Asthma"; Brit Med. J.; 280:646; (1980).
U.S. Appl. No. 10/069,663, filed Nov. 29, 2006; 1.132 Declaration of A.K. Gunnar Aberg, filed Dec. 14, 2006; 3 pages.
Roquet et al.; "Effects of Loratadine on Anti-IgE-Induced Inflammation, Histamine Release, and Leukocyte Recruitment in Skin of Atopics"; Allergy; 50(5); pp. 414-420; Abstract Only; (1995).

* cited by examiner

*Primary Examiner* — Savitha Rao
*Assistant Examiner* — Gregg Polansky
(74) *Attorney, Agent, or Firm* — Cantor Colburn LLP

(57) ABSTRACT

The methods disclosed herein relate to the treatment of dermal disorders, such as for example atopic dermatitis, in dogs, by administering a therapeutically effective amount of racemic norketotifen. Co-administrations with steroids or immunosuppressant drugs are described.

16 Claims, No Drawings

MEDICINAL TREATMENT OF DERMAL DISEASES IN DOGS

CROSS-REFERENCE TO RELATED APPLICATIONS

This application claims priority of provisional application Ser. No. 61/717,240 filed on Oct. 23, 2012, the disclosure of which is hereby incorporated by reference.

TECHNICAL FIELD

The embodiments disclosed herein relate to methods for treatment of inflammatory and allergic dermal diseases in dogs while avoiding side effects that are commonly associated with anti-inflammatory antihistamines.

BACKGROUND

Ketotifen (Zaditen®, Zaditor®, Sandoz, Novartis) is a Generation-1 antihistamine that is mainly used for the treatment of allergic rhinitis. Ketotifen may be the most sedating of all marketed antihistamines and the unusually severe sedative side effects of ketotifen have limited the therapeutic usefulness of the drug. In the USA, ketotifen is only used as eye drops (Zaditor®, Novartis) to alleviate the symptoms of allergic conjunctivitis in humans and does not cause sedation due to the extremely low systemic concentrations of the drug after local administration to the eyes.

Norketotifen, an active metabolite of ketotifen, is an achiral molecule, but has two atropisomers, S-norketotifen and R-norketotifen, as has previously been described in U.S. Pat. Nos. 7,226,934 and 7,557,128. As explained in U.S. Pat. Nos. 7,226,934 and 7,557,128, norketotifen also has a significant sedation effect when studied in the art-accepted mouse model of sedation, and further, the sedative effects were attributed to the R-isomer. It was thus proposed that only the S-isomer could be administered without significant sedation effects.

What is needed are methods of treating inflammatory and dermal disorders without causing sedation or the much feared side effects of the current medications for atopic dermatitis in dogs, which are limited to corticosteroids and immunosuppressant drugs.

SUMMARY

In one aspect, a method for treating pruritic and/or inflammatory dermal disorders in a dog in need of such treatment comprises administering to the dog in need a therapeutically effective amount of norketotifen or a pharmaceutically acceptable salt thereof, wherein the therapeutically effective amount does not produce sedative side effects upon administration to the dog. In further embodiments, norketotifen does not cause the side effects of long-term administration of corticosteroids or the side effects of immunosuppressant drugs.

In another aspect, a method for reducing sedative side effects in the treatment of pruritic and/or inflammatory dermal disorders in a dog in need of such treatment comprises administering to the dog in need a therapeutically effective amount of norketotifen or a pharmaceutically acceptable salt thereof that does not produce sedative side effects upon administration to the dog.

DETAILED DESCRIPTION

The methods disclosed herein relate to the treatment of pruritic and/or inflammatory dermal disorders, such as for example atopic dermatitis, in dogs, by administering an anti-inflammatory and anti-allergic compound, norketotifen and pharmaceutically acceptable salts thereof.

It has previously been found and described that both ketotifen and norketotifen express sedative activity and were therefore not considered to be useful as medications for chronic diseases, such as for example, atopic dermatitis in dogs. Sedation was determined using a mouse model that has previously been used successfully in the development of non-sedating antihistamines, such as loratadine (Claritin®, Schering) and desloratadine (Clarinex®, Schering). It was therefore believed that said mouse model had relevance for evaluating clinical use of the current benzocycloheptathiophene compound that has potent antihistaminic activities. The mouse model clearly demonstrated the sedative effects norketotifen.

It has now surprisingly been found that racemic norketotifen is completely free from sedative effects when tested in dogs, even after administration of high doses of the compound.

The active compound is racemic norketotifen, herein often called RS-norketotifen or nor-ketotifen or just norketotifen. Norketotifen is an achiral molecule, but has two atropisomers, S-norketotifen and R-norketotifen, as has previously been described in U.S. Pat. Nos. 7,226,934 and 7,557,128.

Chemically, norketotifen is (RS)-4-(piperidylidene)-9,10-dihydro-4H-benzo-(4,5)-cyclohepta-(1,2-b) thiophene-10-one. The prefix (RS) can optionally be excluded.

Norketotifen is a metabolite of ketotifen (4-(1-methyl-4-piperidyline)-4H-benzo(4,5)-cyclohepta-(1,2-b) thiophene-10-one). Ketotifen may be the most sedating of all marketed antihistamines and the unusually severe sedative side effects of ketotifen has limited the therapeutic usefulness of the drug, particularly when used for atopic dermatitis in dogs, since very high doses such as 0.5 to 20 mg/kg body weight once or twice daily have to be used in dogs.

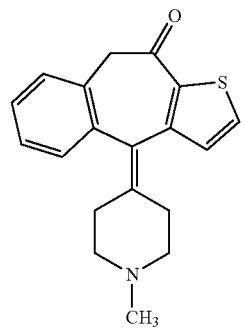

KETOTIFEN

The metabolite norketotifen is formed by demethylation of ketotifen in the liver of mammals:

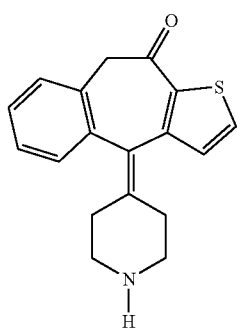

NORKETOTIFEN

Norketotifen can be made from methods known in the art, as described in U.S. Pat. No. 3,682,930, the disclosure of which is hereby incorporated by reference for its teaching of the synthesis of norketotifen.

Except for U.S. Pat. Nos. 7,226,934 and 7,557,128, no publications are known that describe the pharmacodynamic activities of RS-norketotifen. U.S. Patent Publications 2010/0105734 and 2010/0130550 describe the effects of RS-norketotifen when used as eye drops for ocular conjunctivitis and xerophthalmia in humans.

The embodiments disclosed herein provide for the administration of the racemic form of norketotifen or pharmaceutically acceptable acid addition salts of the compound to dogs in need thereof. Norketotifen is ideally suited for the treatment of atopic dermatitis (AD) in dogs, since this compound, has potent anti-inflammatory and antihistaminic effects, and has now, surprisingly, been found to be completely free from sedative side effects in dogs.

Dogs may suffer from various types of skin diseases, which are most often inflammatory and/or pruritic disorders, often classified as allergic disorders. Examples are malassezia (expressing intense pruritus), atopic dermatitis (expressing inflammation and severe pruritus), hot spot (expressing severe pruritus) and seborrheic dermatitis (expressing inflammation and pruritus).

Atopic (allergic) dermatitis in dogs can be caused by various allergens, such as for example food allergens, fleas, bacteria or contact allergens. What may start as seasonal atopic dermatitis often becomes a year-round problem as the dog ages and the skin becomes increasingly sensitive to additional allergens.

Because of the potent anti-inflammatory and antipruritic activities of norketotifen, this substance may be of medicinal value to dogs suffering from a variety of dermal diseases. Of particular importance is the use of norketotifen in dogs suffering from atopic dermatitis, which is a common disease in dogs and is believed to affect between 10 and 20 percent of the 78 million owned dogs in the United States.

In one embodiment, a method for reducing sedative side effects in the treatment of pruritic and/or inflammatory dermal disorders in a dog in need of such treatment comprises administering to the dog in need a therapeutically effective amount of norketotifen or a pharmaceutically acceptable salt thereof that does not produce sedative side effects upon administration to the dog. In one embodiment, treatment is chronic, subchronic, or acute, specifically chronic. As used herein chronic administration is three or more consecutive days of administration, specifically six or more consecutive days of administration. Acute refers to a single administration. Subchronic refers to less than 3 consecutive days of administration.

The embodiments disclosed herein also provide pharmaceutical compositions, which comprise the compound of the invention, formulated together with one or more pharmaceutically acceptable carriers. The pharmaceutical compositions may be specially formulated for oral administration or parenteral administration. The term "parenteral" administration includes intravenous, intraarterial, intramuscular, intraperitoneal, or subcutaneous administration forms.

Pharmaceutical compositions for oral administration of solid dosage forms include capsules and tablets. In solid dosage forms, the active compound may be mixed with one or more pharmaceutically acceptable excipients or carriers (such as for example sodium citrate, dicalcium phosphate), fillers or extenders (such as for example starch, lactose, sucrose, glucose, mannitol, silicic acid), binders (such as for example alginates, carboxymethylcellulose, gelatin, polyvinylpyrrolidone, sucrose, acacia), humectants (such as for example glycerol), solution retarding agents (such as for example paraffin), disintegrating agents (such as for example agar-agar, calcium carbonate, starch, alginic acid, silicates, sodium carbonate), absorption accelerators (such as for example quaternary ammonium compounds), wetting agents (such as for example cetyl alcohol, glycerol monostearate), absorbents (such as for example kaolin, bentonite clay), lubricating agents (such as for example talc, calcium stearate, magnesium stearate, polyethylene glycols, sodium lauryl sulfate), and/or other excipients, such as for example buffering agents.

Liquid dosage forms for oral administration include pharmaceutically acceptable emulsions, solutions, suspensions, syrups and elixirs. The liquid dosage form may also contain commonly known diluents (such as for example water, other solvents, solubilizing agents), emulsifiers (such as for example ethanol, isopropyl alcohol, ethyl carbonate, ethyl acetate, benzyl alcohol, benzyl benzoate, propylene glycol, butylene glycol, dimethyl formamide, oils, oleic acid, glycerol, polyethylene glycols, sorbitan fatty esters, and mixtures thereof.)

The oral compositions may also include other excipients as known to those skilled in the art. The drug can also be administered orally as dog treats.

Pharmaceutical compositions for parenteral injections include pharmaceutically acceptable sterile solutions, dispersions, suspensions, emulsions and sterile powders for reconstitution into sterile injectable solutions or dispersions prior to use. Various carriers, diluents, solvents and vehicles may be used. Fluidity can be maintained by use of coating material such as lecithin, by restricting particle size and by use of surfactants.

Parenteral compositions may also contain excipients such as for example preservatives, wetting agents, emulsifying agents, dispersing agents, isotonic agents, and/or absorption-delaying agents. Absorption-prolonging or absorption-slowing effects may be achieved by injecting a crystalline or amorphous suspension with low water solubility.

The actual dosage levels of active ingredients in the pharmaceutical compositions disclosed herein may be varied so as to obtain the desired therapeutic effect. Thus the amount of drug used varies and will depend on factors such as the administration form, the severity of the disease, the frequency of dosing, and other circumstances (such as general health, age, etc.) known to the caretaker of the dog and the caring veterinarian.

The therapeutically effective oral doses of norketotifen useful for treating dogs with atopic dermatitis (AD) will be determined by the caring veterinarian and are generally higher than doses used for human patients with AD, specifically 0.5 mg/kg to 20 mg/kg bodyweight (calculated as free base) and more specifically 4 mg/kg to 16 mg/kg (calculated as free base), dosed orally as the free base or as a salt, such as for example the hydrochloride salt or the hydrogen fumarate salt, once, twice or more times daily. In one embodiment, the treatment is once daily dosing. The therapeutically effective dose may be administered less than once daily, such as for example two to six times weekly, as determined by the caretaker of the animal or the caring veterinarian. Typically, after therapeutic efficacy has been established, the dosing of norketotifen may be decreased from daily dosing to dosing two to six times weekly.

When used for treatment of dermal disorders, other than atopic dermatitis in dogs, norketotifen can be used in the same doses or in similar doses as described herein for the treatment of atopic dermatitis in dogs. As always, the dose to an individual dog will be modified according to the weight of the animal, the severity of the disease and other circumstances known to the caretaker and the caring veterinarian.

The frequency of dosing and the amount of drug being administered to a particular dog will be determined by the caretaker or a veterinarian and will be based on various clinical factors, such as for example the weight and age of the dog and the severity of the disease of the dog.

The embodiments disclosed herein provide methods for treatment of allergic, and/or immunologic and/or inflammatory skin disorders in dogs, while avoiding the sedating side effects of ketotifen. These methods comprise administering to the canine in need of such treatment, effective amounts of norketotifen or a pharmaceutically acceptable salt thereof, at a dosing frequency to be determined for the individual dog by the caretaker or the caring veterinarian. In one embodiment, dosing frequency is once daily.

In addition to the use of norketotifen as single-drug medication in dogs, embodiments disclosed herein also provide methods for co-administration of norketotifen with at least one drug of the following classes: insecticidal agents, antibacterial agents, antiviral agents, steroids, cyclooxygenase inhibitors, leukotriene antagonists, lipoxygenase inhibitors, inhibitors of one or more cytokines, and immunomodulators, such as for example cyclosporine. The co-administration may be temporary or may be chronically used in the patient dog. The co-administered drug can be administered to the dog separately or can be co-formulated with norketotifen.

Of specific importance is co-administration of norketotifen with an anti-inflammatory steroid, since onset time of the therapeutic activity of norketotifen in dogs suffering from atopic dermatitis may be shortened by said co-administration. For this purpose, norketotifen can be combined with a steroid for the first one to four weeks of therapy. The dose of the steroid depends on the potency of said steroid. High-potency or mid-potency steroids are preferred. As an example, if the mid-potency steroid prednisone, or its metabolite prednisolone, is used in combination with norketotifen, the dose of said steroid is 0.1 to 5.0 mg/kg bodyweight/day and can be combined with an oral dose of norketotifen that is from 0.5 mg/kg bodyweight to 20 mg/kg bodyweight (dosed once or twice daily and calculated as free base). The combination treatment of norketotifen and a steroid like prednisone or prednisolone can be administered to dogs suffering from atopic dermatitis. The combination of norketotifen and a steroid can be administered in double dose for the first one to seven days of therapy. Following the initial treatment of the dog with a combination of norketotifen and a steroid, the continued treatment will consist of norketotifen monotherapy, as described above.

In one embodiment, norketotifen is initially co-administered for one to four weeks of therapy with a steroid in a therapeutically active dose, thereafter followed by monotherapy, wherein norketotifen or a pharmaceutically acceptable salt thereof is administered in an amount of 0.5 mg/kg to 20 mg/kg, dosed once or twice daily and calculated as free base.

Those skilled in the art of pharmacology will realize that steroid-sparing doses will be obtained by co-administration of norketotifen at normal daily doses of between 0.5 mg/kg bodyweight and 20 mg/kg bodyweight dosed once or twice daily and calculated as free base with doses of steroids that are lower than said doses when the steroids are administered as monotherapy. Thus, in dogs suffering from atopic dermatitis, it will be possible to reduce the common therapeutic doses of steroids by 50 percent or more by co-administration of norketotifen at doses ranging from 0.5 mg/kg to 20 mg/kg dosed once or twice daily and calculated as free base. A regular dose of prednisone to dogs suffering from atopic dermatitis depends on the size and age of the dog and the severity of the disease and may range from 1.0 mg/kg bodyweight/day to 2 mg/kg bodyweight/day, or the dose may be even higher. During co-administration with norketotifen the doses of prednisone may be reduced to 0.5 mg/kg bodyweight/day to 1 mg/kg bodyweight/day, or the doses of the steroid may be reduced even further, which reductions are herein considered to be half the regular dose of said steroid.

When used for the treatment of dermal disorders other than atopic dermatitis in dogs, co-administration of norketotifen and a steroid, such as for example prednisone, will result in a steroid-sparing treatment. The same doses of norketotifen and the steroid as described herein for steroid-sparing treatment of atopic dermatitis, can be used. As always, the dose to an individual dog will have to be modified according to the weight of the animal, the severity of the disease and other circumstances known to the caretaker and the caring veterinarian.

Similarly, it will be possible to reduce the doses of an immunosuppressant drug, such as for example cyclosporine with co-administration of norketotifen. Thus, in dogs suffering from atopic dermatitis, it will be possible to reduce common therapeutic doses of an immunosuppressant drug by 50 percent or more by co-administration of norketotifen at normal oral doses, which are ranging from 0.5 mg/kg bodyweight to 20 mg/kg bodyweight, once or twice daily, thereby reducing the potentially very serious side effect of the immunosuppressant drug. As an example, the regular dose of cyclosporine to dogs with atopic dermatitis is 5 mg/kilogram body weight/day until therapeutic efficacy is obtained and thereafter the dose may be decreased to a level where therapeutic activity is maintained in the individual dog. During co-administration with a normal dose of norketotifen, the initial dose of the immunosuppressant drug cyclosporine may be decreased to a range from 1 mg/kilogram bodyweight/day to 3 mg/kilogram bodyweight/day, which is herein called "half the regular dose". The dose of the immunosuppressant drug can be further reduced by dosing the drug every other day, or even more seldom, which is herein called a "further reduced regular dose" of the immunosuppressant. Examples of immunosuppressant drugs are cyclosporine (Atopica®, Novartis), pimecrolimus (Elidel®, Novartis, Meda) and tacrolimus (Protopic®, Astellas Pharma). Immunosuppressant drugs are also called immunomodulating drugs or calcineurin inhibitors.

When used for treatment of other dermal disorders than atopic dermatitis in dogs, co-administration of norketotifen and an immunomodulating drug, such as for example cyclosporine, will use the same doses as described herein for the treatment of atopic dermatitis. As always, the dose to an individual dog will have to be modified according to the drug used, the weight of the animal, the severity of the disease and other circumstances known to the caretaker and the caring veterinarian.

EXAMPLES

Example 1

Antihistaminic Activity In Vitro $H_1$ receptor binding studies were conducted utilizing human recombinant receptors. In the studies shown herein, affinities of the test compounds for histamine $H_1$-receptors were assessed using a binding assay, where [$^3$H] pyrilamine was used as the ligand and the test compounds were used at increasing concentrations. The specific binding of the radioactive ligand to the receptor was defined as the difference between total binding and nonspecific binding, determined in the presence of excess unlabeled ligand. $IC_{50}$ values (the concentration that inhibits 50% of specific binding of the ligand) are determined by non-linear regression analysis of the competition curves. The results are shown in Table 1.

TABLE 1

Antihistaminic activity in vitro

| ANTIHISTAMINE | H-1/IC50 (nM) |
|---|---|
| KETOTIFEN | 2.3 |
| NORKETOTIFEN | 11 |
| LORATADINE (Claritin ®) | 1,500 |
| DESLORATADINE (Clarinex ®) | 16 |
| DIPHENHYDRAMINE (Benadryl ®) | 84 |

Ketotifen is probably the most potent antihistaminic compound ever to be approved as a drug for human use. Norketotifen has less affinity for the histamine-1 receptors than ketotifen, but is more potent than the three reference compounds. Without being held to theory, it is believed that loratadine is a poorly active prodrug and is metabolized in the liver to desloratadine.

Example 2

Antihistaminic Activity In Vivo

Male rats (150-200 g) were fasted overnight and twelve hours after dorsal depilation, the animals were orally pretreated with the test compound(s). Four dorsal test areas were marked with permanent ink, carefully avoiding the area closest to the spine. Sixty minutes after the dosing with the test compound, two intradermal injections of histamine (50 µL; 1.0 mg/ml of histamine di-HCl) were performed, one on each side on the back of the animal. Two intradermal injections of the vehicle for the histamine solution were also performed. Evans blue dye (20 mg/kg) was injected intravenously one minute prior to the intra-dermal injections of histamine and the histamine vehicle. Twenty minutes were allowed for the wheal response to fully develop, whereupon the animals were euthanized and the dorsal skin with the intradermal wheals were deflected. The blue spotted areas were measured in square millimeters and the duplicate wheal areas were averaged. In vehicle-treated animals, the wheal area, on average, was increased by histamine by 94 and 82 mm$^2$ for the vehicles used during the norketotifen and ketotifen experiments, respectively. The inhibition was calculated in percent difference from said baseline values. The results are shown in Table 2.

TABLE 2

Antihistaminic activity in vivo

| Test compound Dose (mg/kg) | Histamine (mm$^2$) | Saline (mm$^2$) | Histamine effect (mm$^2$) | Inhibition (%) |
|---|---|---|---|---|
| Vehicle* | 116 ± 5 | 22 ± 1 | 94 | — |
| Vehicle** | 107 ± 4 | 25 ± 1 | 82 | — |
| Ketotifen; 1.0 | 68 ± 6 | 21 ± 2 | 47 | 43 |
| Ketotifen; 10 | 24 ± 2 | 22 ± 3 | 2 | 98 |
| Norketotifen; 1.0 | 114 ± 8 | 22 ± 1 | 92 | 2 |
| Norketotifen; 10 | 39 ± 2 | 22 ± 1 | 17 | 82 |
| Norketotifen; 50 | 10 ± 1 | 12 ± 1 | 0 | 100 |
| DPH; 10*** | | | | 31 |

*Vehicle for norketotifen expts
**Vehicle for ketotifen expts
***DPH = diphenhydramine (Benadryl ®)

When plotted, ketotifen was found to be 2 to 3 times more potent than norketotifen as an antihistamine in these in vivo studies. Norketotifen was significantly more potent than diphenhydramine.

Example 3

Anti-Inflammatory Effects In Vitro

In these studies, histamine was the marker compound for inflammatory mediators that are released from mast cells and other pro-inflammatory cells in patients with atopic inflammatory diseases. The inhibition of stimulated histamine release from human leukocytes (buffy coat) by test articles was studied. Leukocytes were obtained from healthy volunteers and histamine release was induced by incubation (20 min/37° C.) with the calcium ionophore A23187 (5 µM) in the presence or absence of a test article. Histamine was analyzed by enzyme-immune assays, using commercially available kits and a microplate reader (MRX, Dynatech). The test articles were evaluated, in duplicate, at five concentrations. The results are shown in Table 3.

TABLE 3

Inhibition of inflammatory mediator (histamine) release; IC50 (µM)

| Test article | IC50 (µM) |
|---|---|
| Ketotifen | 91 |
| Norketotifen | 9.2 |

Norketotifen was approximately 10 times more potent than ketotifen as an inhibitor of histamine release from pro-inflammatory cells.

Example 4

Anti-Inflammatory Effects In Vivo

In order to investigate the effects of the test compounds in dermal inflammation, a croton oil model was used as is known in the art. This test consists of topical application of 20 µl of 1.0% croton oil to each ear of male mice, weighing 28-32 g. The weight of untreated ears of these animals is 30-32 mg. Application of the croton oil results in an inflammatory response. The weight of croton oil-treated ears was determined and the percent increase in ear weight is calculated. Test articles were dosed systemically (ip).

The effects of 10 mg/kg of RS-ketotifen and RS-norketotifen at 90 and 120 minutes after administration of test articles are shown in the following table. All results represent mean ear weights (±S.E.M.) from 10 ears. The results are shown in Table 4.

TABLE 4

Anti-inflammatory effects in vivo

| Test Article | Average Ear weight (mg) ± SEM | |
|---|---|---|
| | 90 min | 120 min |
| Control | 48 ± 2 | 51 ± 2 |
| Ketotifen | 37 ± 1 | 42 ± 1 |
| Norketotifen | 34 ± 1 | 40 ± 1 |

Both test compounds demonstrated dermal anti-inflammatory effects. All or part of the anti-inflammatory effect of ketotifen is assumed to be due to norketotifen that is formed as a metabolite of ketotifen in the rodents.

Example 5

Sedative Effects in Mice

The sedation study in mice has previously been used by Schering in the loratadine project (U.S. Pat. No. 4,659,716, 1987) and by Sepracor in the desloratadine project (U.S. Pat. No. 5,595,997), which patents are hereby included by reference for their disclosure of sedation studies. In short, physostigmine (1.0 mg/kg to 2.0 mg/kg, s.c.) generally results in 100% lethality when given to groups of mice (10 mice/group) transferred into a small volume of space. Mice administered a sedating drug prior to the physostigmine injection are protected from the stress and survive. In the present study, test compounds were given orally 60 minutes prior to physostigmine injection. The number of surviving (sedated) mice was counted 30 minutes after injection of the physostigmine dose. Results are shown from tests that were performed between the years 1997 and 2009 in Table 5.

TABLE 5

Sedative effects in mice

| | Oral dose (mg/kg) | Sedated animals |
|---|---|---|
| VEHICLE | — | 0/10 |
| NORKETOTIFEN | 83 | 3/10 |
| NORKETOTIFEN | 100 | 3/10 |
| NORKETOTIFEN | 150 | 3/10 |
| NORKETOTIFEN | 180 | 6/10 |
| S-NORKETOTIFEN | 100 | 0/10 |
| S-NORKETOTIFEN | 150 | 0/10 |
| R-NORKETOTIFEN | 100 | 3/10 |
| R-NORKETOTIFEN | 150 | 3/10 |
| KETOTIFEN (Zaditen ®; Gen-1) | 25 | 5/10 |
| KETOTIFEN (Zaditen ®; Gen-1) | 50 | 8/10 |
| KETOTIFEN (Zaditen ®; Gen-1) | 100 | 10/10 |
| CYPROHEPTADINE (Periactin ®; Gen-1) | 100 | 9/10 |
| PYRILAMINE (Mepyramine ®; Gen-1) | 100 | 8/10 |
| HYDROXYZINE (Atarax ®; Gen-1) | 100 | 9/10 |
| DIPHENHYDRAMINE (Benadryl ®; Gen-1) | 50 | 5/10 |
| DIPHENHYDRAMINE (Benadryl ®; Gen-1) | 100 | 8/10 |
| ASTEMIZOLE (Hismanal ®; Gen-2) | 100 | 1/10 |
| NORASTEMIZOLE (Soltara ™; Gen-2) | 100 | 0/10 |
| LORATADINE (Claritin ®; Gen-2) | 150 | 1/10 |
| DESLORATADINE (Clarinex ®; Gen-2) | 150 | 0/10 |
| TERFENADINE (Seldane ®; Gen-2) | 150 | 0/10 |
| FEXOFENADINE (Allegra ®; Gen-2) | 150 | 0/10 |

Gen-1 = Generation-1 (sedating antihistamines)
Gen-2 = Generation-2 (non-sedating antihistamines)

All registered Generation-1 antihistamines were sedating in mice and all registered Generation-2 antihistamines were free from sedation, using the physostigmine lethality test. Racemic norketotifen expressed sedative activity in this test system.

Example 6

Sedative Effects in Dogs

Sedation studies in dogs were performed according to a cross-over protocol, where the dogs were administered once daily the test articles orally at a dose of 20 mg/kg bodyweight that in a previous toxicology study was marginally toxic in dogs with equal plasma concentrations of R-norketotifen and S-norketotifen.

The test articles were administered in gelatin capsules and vehicle-capsules were empty. All dogs were healthy beagles (four males and two females), age 24-36 months, weighing 7.8-10.6 kg. The dogs were dosed at 9-10 AM and had been fasted overnight before dosing. There was a washout period of at least three days in all dogs between the tests. All assessments of sedation/sleepiness were made by a qualified (D.V.M.) scientist with extensive experience (>15 years) in studies with conscious laboratory dogs. The test articles were in the form of hydrogen fumarate salts.

It had previously been observed that dogs rarely express sedation in response to oral administration of benzocycloheptathiophene compounds on the first day of dosing and the dogs were therefore administered the test articles for three consecutive days. The results are shown in Table 6.

TABLE 6

Sedative effects in dogs

| Treatment | Frequency of sedation | | |
|---|---|---|---|
| (20 mg/kg/day) | DAY 1 | DAY 2 | DAY 3 |
| Ketotifen | 0/6 | 5/6 | 5/6 |
| Norketotifen | 0/6 | 0/6 | 0/6 |
| Vehicle | 0/6 | 0/6 | 0/6 |

The test results demonstrate that ketotifen causes sedation in dogs, which is not surprising, since diphenhydramine (Benadryl®) also causes sedation in dogs.

Surprisingly, norketotifen did not cause sedation in dogs, which is contrary to the results from earlier animal studies using the mouse physostigmine model, which test method has been considered to be of high predictive value. To our knowledge, this is the first study that has been performed to specifically study sedative side effects of norketotifen in dogs and it has now surprisingly been found that racemic norketotifen is completely free from sedative effects in this species.

The sedative effects of ketotifen have been reported from tests using the mouse physostigmine sedation tests. Sedative side effects of ketotifen, expressed as effect on the sleep pattern in dogs, have been published. Sedative side effects of norketotifen are reported herein and have been reported from tests using the physostigmine test method. To our knowledge, norketotifen has never been administered to dogs suffering from any disease, including atopic dermatitis.

Example 7

Toxicological Effects

Acute toxicological studies were performed in rats (Sprague-Dawley; M and F; 200-250 grams). The animal-sparing Up-and-Down Procedure (FDA, OECD) was used. Both oral and intravenous toxicity tests were performed.

The acute toxicity, expressed as estimated LD50 and calculated in mg/kg body weight of norketotifen and ketotifen are shown in Table 7. Both compounds were administered as hydrogen fumarate salts.

TABLE 7

Toxicological effects

| TEST SYSTEM | Acute toxicity (estimated LD50) mg/kg | |
|---|---|---|
| | NORKETOTIFEN | KETOTIFEN |
| RAT; intravenous | 10-15 | 5-10 |
| RAT; oral | 1500-2000 | <300 |

Norketotifen is significantly less toxic than ketotifen after intravenous or oral administration.

Example 8

Exemplary Oral Dosage Formulation

TABLE 8

Tablet formulations

| Ingredient | Amount per tablet | Amount per batch |
|---|---|---|
| Norketotifen | 40 mg | 400 g |
| Microcrystalline cellulose | 30 mg | 300 g |
| Lactose | 70 mg | 700 g |
| Calcium stearate | 2 mg | 20 g |
| FD&C Blue #1 Lake | 0.03 mg | 300 mg |

The active ingredient is blended with the lactose and cellulose until a uniform blend is formed. The blue lake is added and further blended. Finally, the calcium stearate is blended in, and the resulting mixture is compressed into tablets using for example a 9/32-inch (7 mm) shallow concave punch. Tablets of other strengths may be prepared by altering the ratio of active ingredient to the excipients or to the final weight of the tablet.

Those skilled in the art realize that oral formulations can also be in the form of for example a capsule, a dog-treat or a liquid formulation.

As used herein, the terms "pharmaceutically acceptable salts" or "a pharmaceutically acceptable salt thereof" refer to norketotifen salts, which have been prepared from pharmaceutically acceptable non-toxic acids. Exemplary pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. The hydrochloride salt and the hydrogen fumarate salt are particularly preferred.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for treating pruritic and/or inflammatory dermal disorders in a dog in need of such treatment, comprising orally administering to the dog in need a therapeutically effective amount of RS-norketotifen or a pharmaceutically acceptable salt thereof, wherein the therapeutically effective amount does not produce sedative side effects upon administration to the dog.

2. The method of claim 1, wherein said dermal disorder is canine atopic dermatitis.

3. The method according to claim 1, wherein the amount of said RS-norketotifen or pharmaceutically acceptable salt thereof is 0.5 mg/kg bodyweight to 20 mg/kg bodyweight, expressed as free base and dosed once or twice daily.

4. The method according to claim 3, wherein said amount of RS-norketotifen is initially co-administered for one to four weeks of therapy with a corticosteriod in a therapeutically active dose, thereafter followed by monotherapy with RS-norketotifen.

5. The method according to claim 4, wherein said corticosteriod is prednisone or prednisolone administered at a daily dose of 0.1 mg/kilogram bodyweight to 1.0 mg/kilogram bodyweight.

6. The method according to claim 3, wherein said norketotifen is co-administered with a therapeutically effective dose of a corticosteroid.

7. The method according to claim 3, wherein said amount of RS-norketotifen is co-administered with an immunosuppressant drug, wherein the daily dose of the immunosuppressant drug is reduced by half the regular dose of said immunosuppressant.

8. The method of claim 7, wherein said immunosuppressant is cyclosporine dosed at 1.0 mg/kg bodyweight/day to 3.0 mg/kg bodyweight/day.

9. A method for reducing sedative side effects in the treatment of pruritic and/or inflammatory dermal disorders in a dog in need of such treatment, comprising orally administering to the dog in need a therapeutically effective amount of RS-norketotifen or a pharmaceutically acceptable salt thereof that does not produce sedative side effects upon administration to the dog.

10. The method of claim 9, wherein said dermal disorder is canine atopic dermatitis.

11. The method according to claim 9, wherein the amount of said RS-norketotifen or pharmaceutically acceptable salt thereof is 0.5 mg/kg bodyweight to 20 mg/kg bodyweight, expressed as free base and dosed once or twice daily.

12. The method according to claim 11, wherein said amount of RS-norketotifen is initially co-administered for one to four weeks of therapy with a corticosteriod in a therapeutically active dose, thereafter followed by monotherapy with RS-norketotifen.

13. The method according to claim 12, wherein said steroid is prednisone or prednisolone administered at a daily dose of 0.1 mg/kilogram bodyweight to 1.0 mg/kilogram bodyweight.

14. The method according to claim 11, wherein said RS-norketotifen is co-administered with a therapeutically effective dose of a steroid.

15. The method according to claim 11, wherein said amount of RS-norketotifen is co-administered with an immunosuppressant drug, wherein the daily dose of the immunosuppressant drug is reduced by half the regular dose of said immunosuppressant.

16. The method of claim 15, wherein said immunosuppressant is cyclosporine dosed at 1.0 mg/kg bodyweight/day to 3.0 mg/kg bodyweight/day.

* * * * *